US010639231B2

(12) United States Patent
Fryman et al.

(10) Patent No.: US 10,639,231 B2
(45) Date of Patent: May 5, 2020

(54) INTERCOURSE ASSISTANCE DEVICE

(71) Applicant: Ovid, LLC, Canton, GA (US)

(72) Inventors: Julie Fryman, Canton, GA (US); Michelle Larue, Roswell, GA (US)

(73) Assignee: Ovid, LLC, Canton, GA (US)

( * ) Notice: Subject to any disclaimer, the term of this patent is extended or adjusted under 35 U.S.C. 154(b) by 161 days.

(21) Appl. No.: 15/848,119

(22) Filed: Dec. 20, 2017

(65) Prior Publication Data

US 2018/0168920 A1  Jun. 21, 2018

Related U.S. Application Data

(63) Continuation of application No. 14/809,993, filed on Jul. 27, 2015, now Pat. No. 9,877,890.

(60) Provisional application No. 62/028,854, filed on Jul. 25, 2014.

(51) Int. Cl.
*A61F 5/00* (2006.01)
*A61H 19/00* (2006.01)
*A61F 5/41* (2006.01)

(52) U.S. Cl.
CPC ............ *A61H 19/50* (2013.01); *A61H 19/32* (2013.01); *A61F 2005/414* (2013.01); *A61H 2201/01* (2013.01)

(58) Field of Classification Search
CPC .................. A61H 19/32; A61H 19/50
USPC ........................ 600/38–41; 128/844
See application file for complete search history.

(56) References Cited

U.S. PATENT DOCUMENTS

| 6,298,852 | B1 | 10/2001 | Manning |
| 6,306,080 | B1 | 10/2001 | Mitchell et al. |
| 7,926,489 | B2 | 4/2011 | Anderson et al. |
| 8,007,431 | B2 | 8/2011 | Miller et al. |
| 9,877,890 | B2 * | 1/2018 | Fryman ............... A61H 19/50 |
| 2003/0024536 | A1 | 2/2003 | Bagby |
| 2007/0283965 | A1 * | 12/2007 | Foks .................. A61H 19/50 |
| | | | 128/845 |
| 2011/0146695 | A1 | 6/2011 | Taouil |

FOREIGN PATENT DOCUMENTS

| CN | 201147402 Y | 11/2008 |
| CN | 202526374 U | 11/2012 |

* cited by examiner

*Primary Examiner* — John P Lacyk
(74) *Attorney, Agent, or Firm* — Merchant & Gould P.C.

(57) ABSTRACT

An intercourse assistance device for reducing the length of a penis that enters a vagina. The intercourse assistance device has a support body with a front side and a rear side. The support body is made of resistantly-rigid material. The device includes a region of deformably-soft material monolithically positioned centrally within the support body. The deformably-soft material is adapted to deform when in contact with the penis. The device also includes a reflexively-closable opening cut out from the region of reflexively-deformable material. The opening is adapted to removably receive the penis.

13 Claims, 6 Drawing Sheets

INTERCOURSE ASSISTANCE DEVICE

This application is a continuation of U.S. patent application Ser. No. 14/809,993, filed Jul. 27, 2015, now U.S. Pat. No. 9,877,890, issued Jan. 20, 2018, which claims benefit of U.S. Provisional Ser. No. 62/028,854, filed Jul. 25, 2014, which applications are incorporated herein by reference. To the extent appropriate, a claim of priority is made to the above disclosed applications.

BACKGROUND

Dyspareunia, or painful intercourse, can be caused by many physical and psychological conditions. It can occur just before, during, or after intercourse. Painful intercourse may be caused by endometriosis, radiation, chemotherapy, ovulation, menstruation, pregnancy, a previous surgery, scar tissue, menopause, and vaginal atrophy. These conditions may lead to less elastic vaginal tissue, vaginal shortening, and swelling. All of these vaginal changes may lead to painful intercourse.

Dyspareunia may also be a result of the length of a man's penis, more specifically the length of the penis with regard to his partner's vagina. When the man's penis is long, pain can occur during penetrations. However, for completely healthy women, increased length of the penis may result in the lower portion of the uterus, or cervix, being contacted, especially during thrusting that can be extremely painful.

For these reasons, there exists a need for improvements that would help reduce dyspareunia.

SUMMARY

Aspects of the present description relate to an intercourse assistance device for reducing the length of a penis that enters a vagina. The intercourse assistance device has a support body with a front side and a rear side. The support body is made of resistantly-rigid material. The device includes a region of deformably-soft material monolithically positioned centrally within the support body. The deformably-soft material is adapted to deform when in contact with the penis. The device also includes a reflexively-closable opening cut out from the region of reflexively-deformable material. The opening is adapted to removably receive the penis.

Further aspects of the present description relate to a method for reducing the length of a penis that enters a vagina. The method includes receiving the penis within a reflexively-closable opening cut out from a volume of reflexively-deformable material. The volume is surrounded by a support body comprising a front side and a rear side separated by a predefined height. The height is defined by the length by which the penis is reduced.

DESCRIPTION OF EXAMPLE EMBODIMENTS

Figure 1:
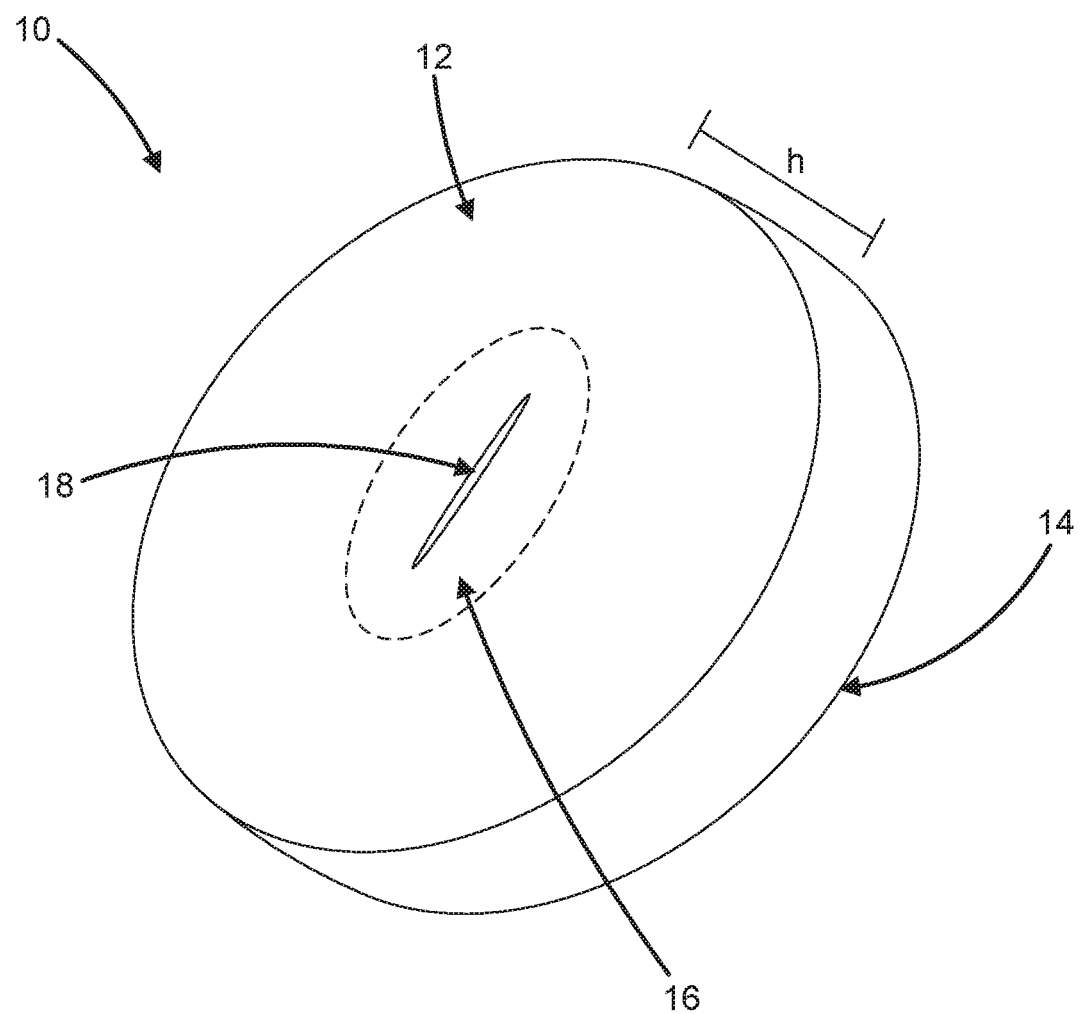
FIG. 1 is a perspective view of an intercourse assistance device according to a first example embodiment of the invention.
Figure 2:
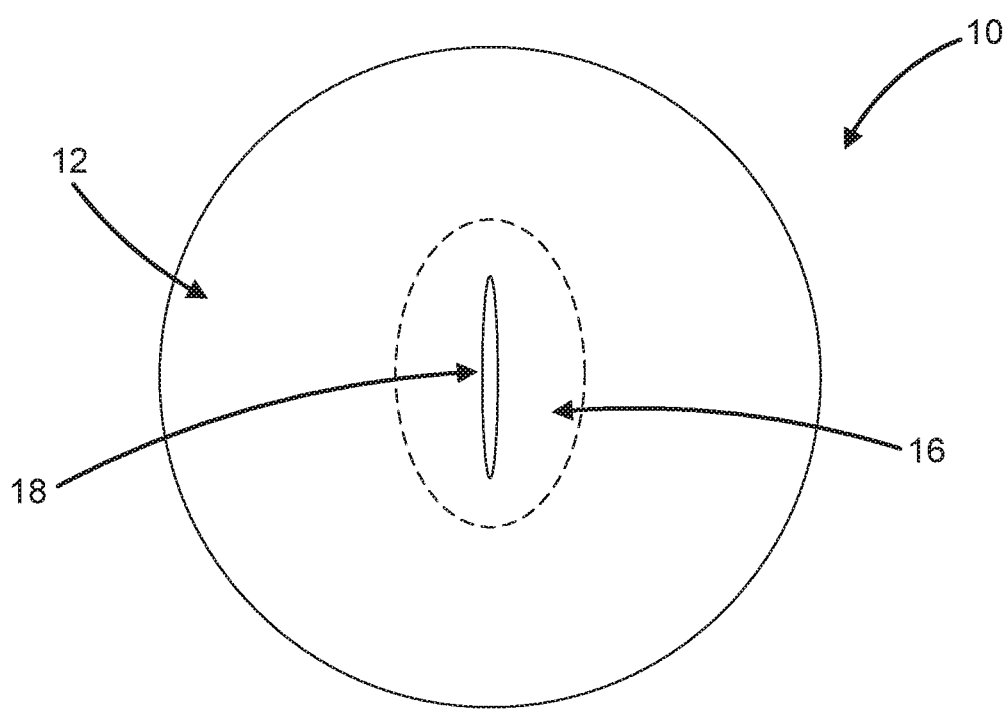
FIG. 2 is a view of the front side of the intercourse assistance device of FIG. 1, showing the slit in a closed relaxed state.
Figure 3:
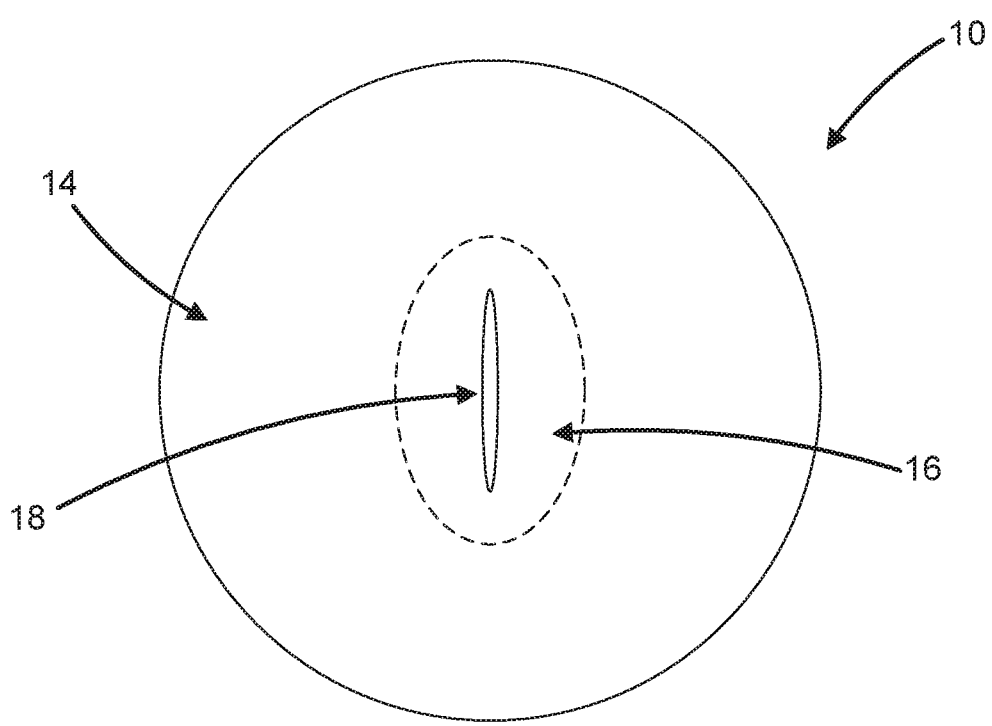
FIG. 3 is a view of the rear side of the intercourse assistance device of FIG. 1, showing the slit in a closed relaxed state.
Figure 4:
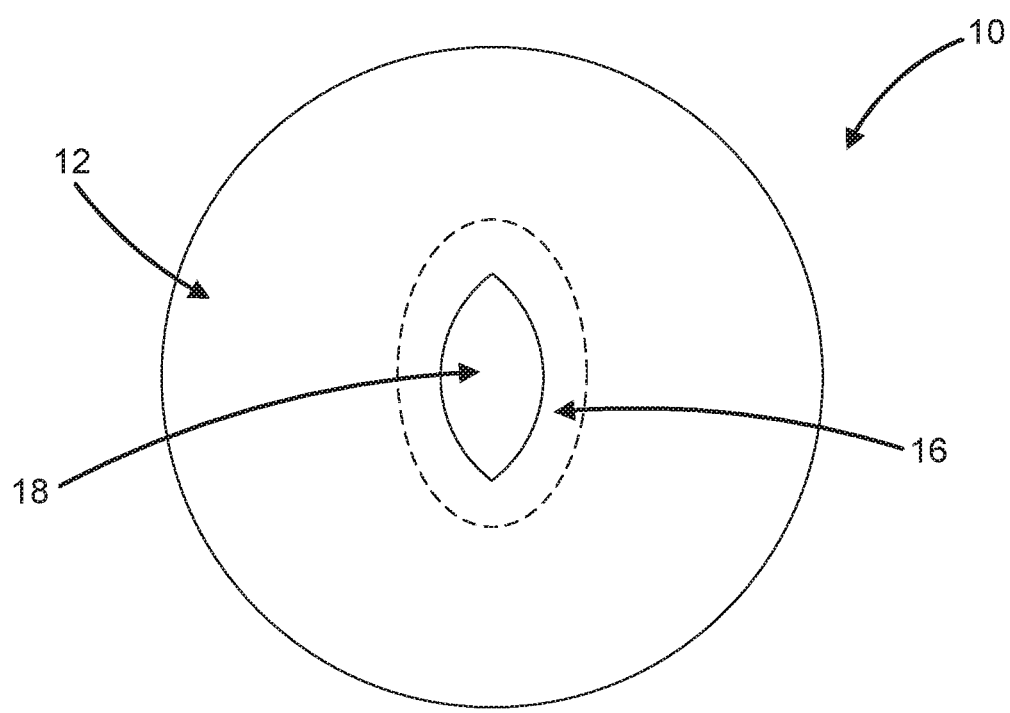
FIG. 4 is a view of the front side of the intercourse assistance device of FIG. 1, showing the slit in an open state.
Figure 5:
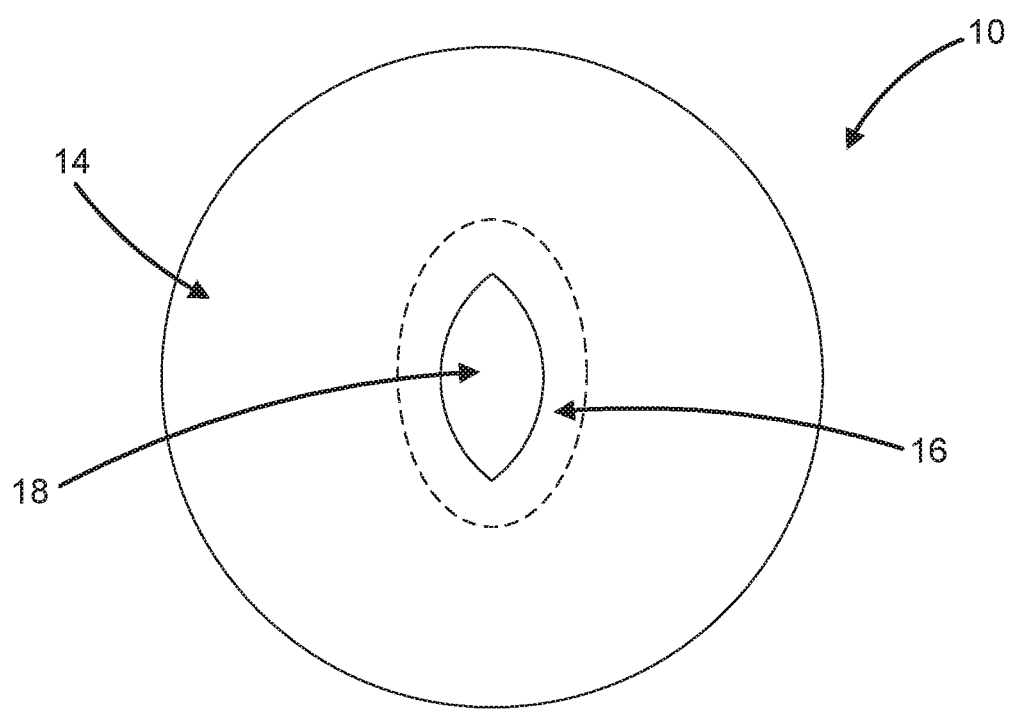
FIG. 5 is a view of the rear side of the intercourse assistance device of FIG. 1, showing the slit in an open state.

According to an example embodiment, the intercourse assistance device is positioned to rest at the base of the penis. When in place at the base of the penis, the device reduces the length of the penis that can fully penetrate a vagina during sexual intercourse.

As depicted in FIGS. 1-5, the example device 10 can be disc-shaped (or ring shaped) with a front side 12, a rear side 14 and a circumferential outer wall extending therebetween. The diameter of the device 10 is uniform between the front side 12 and the rear side 14. This diameter of the device 10 can be between about 5 and about 9 centimeters, preferably between about 6 and about 8 diameters, and most preferably about 7 diameters. The diameter of the device 10 should be great enough to prevent entry into the vagina. Alternatively, the device 10 can have a shape other than circular, for example oval, or oblong. The height h of the circumferential wall can be between 1 and 6 centimeters, preferably between about 2 an about 5 centimeters and most preferably between about 3 and about 4 centimeters. The height h of the device 10 should be great enough to reduce the distance of entry of the penis into the vagina.

An openable slit or opening 16 is positioned centrally and extends between the front side 12 and the rear side 14, forming a channel or passageway therethrough. The slit or opening 18 is aligned along a central axis or equator of the device and in storage has a relaxed/closed length of preferably less than about 1 centimeter. The slit or opening 18 extends within a region 16 of elastomeric soft and resiliently deformable material that uniformly extends between the front side 12 and the rear side 14. This region 16 can have a circumferential area, or an alternatively effective shape. The slit or opening 18 is cut out or formed from this soft and resiliently deformable material to allow this slit or opening to be spread open during use with the insertion of a penis therethrough (FIGS. 4-5) and then reflexively close (FIGS. 2-3) in a relaxed state of non-use. Surrounding this soft region 16, the remainder of the device 10 is formed of firmer elastomeric material that uniformly extends between the front side 12 and the rear side 14 to prevent collapse during use. This firm material can be firm enough to provide support during use and provide resistance preventing insertion of a penis too far into a vagina. Preferably the entire device 10 is manufactured of unitary monolithic construction, seamless, has rounded edges and smooth surfaces to prevent chaffing during use.

The device 10 can be manufactured of elastomeric material that is medical-grade, non-porous, non-phthalate, and hypo-allergenic. An example material can include medical-grade rubber, including neoprene, GR-S, silicone, nitrile, butyl compounds, polyacrylate, and urethane elastomer. The device 10 can be manufactured through injection-molding.

In use, the penis (not shown) is inserted into the slit or opening 18 and extends completely through the channel to exit out of the opposite side. The soft material in the region 16 allows the slit or opening 18 to open or expand (FIGS. 4-5) when the penis is inserted. The device 10 is then pushed to the base of the penis during use. The height h of the circumferential wall is designed to reduce the length of the penis that enters the vagina when the device 10 is positioned at the base of the penis.

Upon completion of intercourse, the penis (not shown) is removed from within the slit or opening 18 and the region 16 of soft material reflexively closes the slit or opening.

Figure 6:
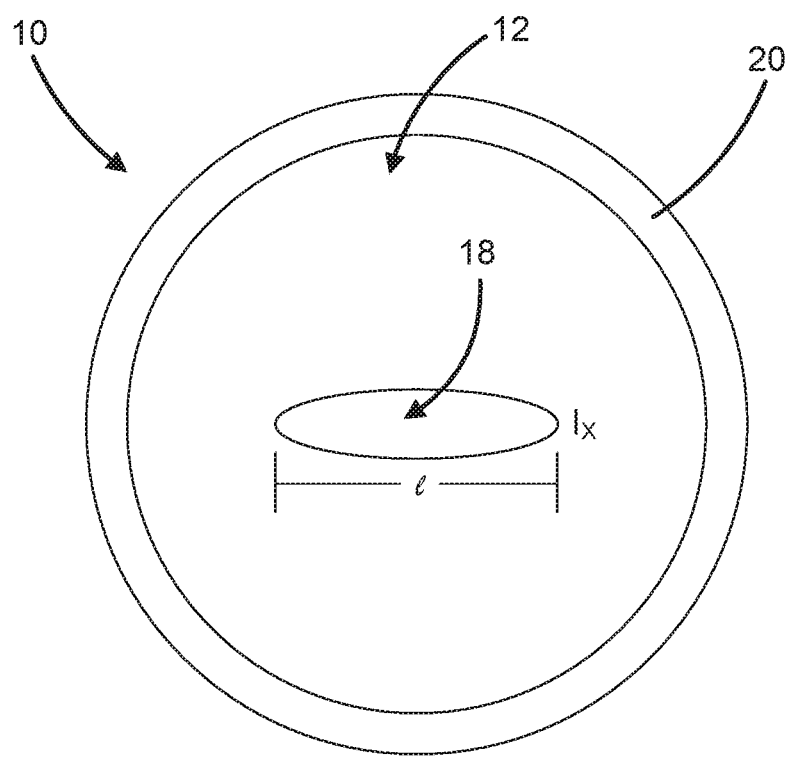
FIG. 6 is a top view of an intercourse assistance device according to a second example embodiment of the invention.
Figure 7:
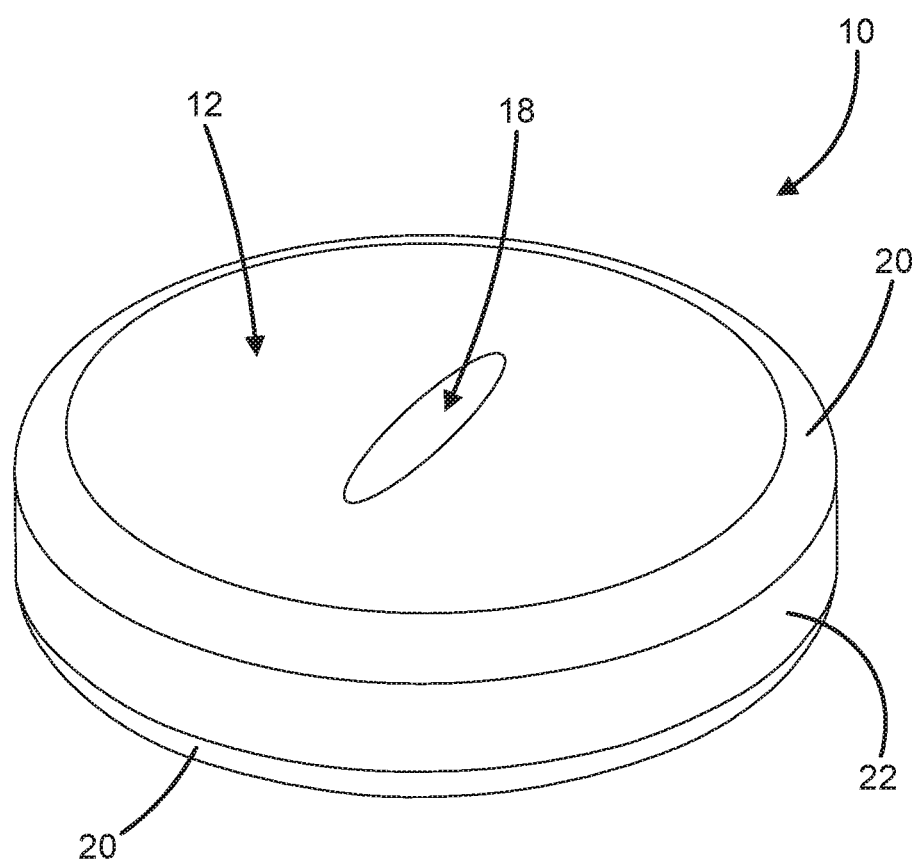
FIG. 7 is a perspective view of the intercourse assistance device of FIG. 6.

FIGS. 6-7 depict the device 10 shown in FIGS. 1-5 with additional features. The device 10 can have chamfered edges 20 between the top 12 surface and sidewall 22, and between the sidewall 22 and the bottom surface 14 (not shown). As depicted, the height of the device 10 from the top surface 12 to the bottom surface 14 (not shown) can be about 20 mm. Additionally, as depicted in a relaxed non-use state, the receiver slit opening 18 can have an elongated shape with a length L of between about 30 mm and about 33 mm, more preferably about 31.75 mm and not to exceed 32 mm. The receiver slit opening 18 can have width X of between about 6 mm and about 7 mm, more preferably about 6.35 mm not to exceed 7 mm.

Although applicant has described applicant's preferred embodiments of this invention, it will be understood that the broadest scope of this invention includes modifications such as diverse shapes, sizes, and materials. Such scope is limited only by the below claims as read in connection with the above specification. Further, many other advantages of applicant's invention will be apparent to those skilled in the art from the above descriptions and the below claims.

What is claimed is:

1. An intercourse assistance device, the device comprising a support body comprising a deformable material extending between a front side and a rear side, the support body having a reflexively deformable opening extending from the front side to the rear side, wherein the support body comprises a region of firm material that surrounds the reflexively deformable opening, the region of firm material being adapted to provide a resistant force.

2. The device of claim 1, wherein the reflexively deformable opening is positioned centrally within the geometry of the front side and the rear side of the support body.

3. The device of claim 1, wherein the deformable material is uniform between the front side and the rear side of the support body.

4. The device of claim 1, wherein the deformable material is resiliently soft.

5. The device of claim 1, wherein the reflexively deformable opening comprises a first cross-sectional geometry in-use and a different second cross-sectional geometry during non-use.

6. The device of claim 1, wherein the reflexively deformable opening defines cross-sectional dimensions including a length and a different width.

7. The device of claim 6, wherein the length dimension is up to about 4 times greater than the width dimension.

8. The device of claim 1, wherein the reflexively deformable opening is reflexively closeable.

9. An intercourse assistance device, the device comprising a support body having a reflexively changeable opening extending between a front side and rear side, the reflexively changeable opening comprising an in-use cross-sectional geometry and a different at-rest cross-sectional geometry, wherein the reflexively changeable opening is positioned within a volume of deformable material, and wherein the support body comprises a region of firm material that surrounds the reflexively changeable opening, the region of firm material being adapted to provide a resistant force.

10. The device of claim 9, wherein the reflexively changeable opening comprises a length dimension and a different width dimension.

11. The device of claim 10, wherein the width dimension comprises an in-use amount and a different at-rest amount.

12. The device of claim 10, wherein the length dimension is greater than the width dimension.

13. The device of claim 12 wherein the length dimension is up to about 4 times greater than the width dimension.

* * * * *